(12) United States Patent
Vogel

(10) Patent No.: US 8,349,598 B2
(45) Date of Patent: Jan. 8, 2013

(54) LASER DOSIMETRY FOR THE OPTOPERFORATION OF SINGLE CELLS

(75) Inventor: Alfred Vogel, Lübeck (DE)

(73) Assignee: Universitat Zu Lubeck, Lubeck (DE)

( * ) Notice: Subject to any disclaimer, the term of this patent is extended or adjusted under 35 U.S.C. 154(b) by 575 days.

(21) Appl. No.: 12/523,646

(22) PCT Filed: Jan. 9, 2008

(86) PCT No.: PCT/DE2008/000026
§ 371 (c)(1),
(2), (4) Date: Oct. 2, 2009

(87) PCT Pub. No.: WO2008/086772
PCT Pub. Date: Jul. 24, 2008

(65) Prior Publication Data
US 2010/0021983 A1    Jan. 28, 2010

(30) Foreign Application Priority Data
Jan. 18, 2007 (DE) .......... 10 2007 003 600

(51) Int. Cl.
*C12N 13/00* (2006.01)
(52) U.S. Cl. ............... 435/173.5; 435/173.1; 435/173.4; 435/446; 435/448; 435/460
(58) Field of Classification Search .................. None
See application file for complete search history.

(56) References Cited

U.S. PATENT DOCUMENTS

| 2001/0020164 A1 * | 9/2001 | Papademetriou et al. ........ 606/7 |
| 2006/0111697 A1 | 5/2006 | Brinkmann et al. | |

OTHER PUBLICATIONS

Schaffer, CB et al. Dynamics of femtosecond laser-induced breakdown in water from femtoseconds to microseconds. Optics Express. 2002. 10(3): 196-203.*
Chen et al., "Shock-Wave Propagation and Cavitation Bubble Oscillation by Nd:YAG Laser Ablation of a Metal in Water", Applied Optics, vol. 43, No. 16, 2004, pp. 3251-3257.
Rau et al., "Pulsed Laser Microbeam-Induced Cell Lysis: Time-Resolved Imaging and Analysis of Hydrodynamic Effects", Biophysical Journal, vol. 91, Jul. 2006, pp. 317-329.
Rau et al., "Investigation of Laser-Induced Cell Lysis Using Time-Resolved Imaging", Applied Physics Letters, vol. 84, No. 15, Apr. 2004, pp. 2940-2942.
Stevenson et al., "Femtosecond Optical Transfection of Cells: Viability and Efficiency", Optics Express, vol. 14, No. 16, Aug. 2006, pp. 7125-7133.
Tuziuti et al., "Spatial Study on a Multibubble System for Sonochemistry by Laser-Light Scattering", Ultrasonics Sonochemistry, No. 12, 2005, pp. 73-77.
Vogel et al., "Mechanisms of Femtosecond Laser Nanosurgery of Cells and Tissues", Applied Physics B, No. 81, 2005, pp. 1015-1047.
Neumann, "Mikroskopische Untersuchungen zur laser-induzierten Blasenbildung und -dynamik an absorbierrenden Mikropartikeln", Dissertation, University of Lubeck, 2005.

* cited by examiner

*Primary Examiner* — Allison Ford
*Assistant Examiner* — Susan E Fernandez
(74) *Attorney, Agent, or Firm* — Diederiks & Whitelaw, PLC

(57) ABSTRACT

A method of optoperforation of the membrane of a cell by application of laser pulses characterized by focusing the pulsed laser beam onto the cell membrane to be perforated, applying a series of laser pulses of predetermined pulse energy, measuring the oscillation time of the bubbles formed in the laser focus from the change in laser intensity of a test laser beam transmitted through the laser focus and caused by the bubbles in the laser focus, and increasing the pulse energy to a level at which the oscillation time of the bubbles attains a predetermined value.

19 Claims, 2 Drawing Sheets

LASER DOSIMETRY FOR THE OPTOPERFORATION OF SINGLE CELLS

CROSS-REFERENCE TO RELATED APPLICATION

This application represents a National Stage application of PCT/DE2008/000026 entitled "Laser Dosimetry for the Laser Perforation of Individual Cells" filed Jan. 9, 2008, pending.

BACKGROUND OF THE INVENTION

The introduction of foreign materials which is not membrane-permeable (for example nucleic acid molecules, chromosomes, organelles, nanoparticles, proteins, dyes or active pharmaceutical agents) into cells is a widespread cell biology problem. The targeted introduction of the substances into selected single cells within a cell population is particularly difficult.

Whereas easy-to-handle methods for permeating the cell membrane and, hence, methods widely used in laboratories, for example, electroporation (namely the transient permeabilization of the cell membrane by voltage pulses) or the use of liposomes (lipid vesicles containing the foreign material that is to be introduced and which coalesce with the cell membrane) as a rule act simultaneously and nonspecifically on a multitude of cells, until a short time ago virtually only the method of microinjection was available for the manipulation of single cells, a method that is costly in terms of the required equipment and highly demanding in terms of the handling. By this method, the foreign material is injected directly into the cell nucleus or the cytoplasm of the cell with the aid of a microcapillary. The method has an efficiency close to 100%. Only relatively few cells, however, can be handled within a practical length of time.

In past years, progress in laser nanosurgery has led to the development of laser-mediated permeabilization of the cell membrane (optoperforation, also referred to as laser perforation or photoperforation) to permit in this manner the introduction of foreign material into selected single cells. By means of an appropriate microscope arrangement, for example, as the one described by Stevenson et al. (2006, Optics Express, Vol. 14, No. 16, pp. 7125-33), the cell membrane of single cells can be irradiated by pulsed, laser radiation. At the site of the incidence of the laser radiation on the cell membrane, cavitation bubbles are formed provided the radiation intensity is sufficient. In such a case, the bubbles are generated in a nominally transparent medium by multiphoton absorption, the two-photon absorption playing an important role (see Stevenson et al.). Meanwhile, it is assumed that when single laser pulses or a series of pulses with a repetition rate of $\leq 1$ MHz are used, the target cell can effectively take up the foreign material to be introduced only when these cavitation bubbles are formed during the irradiation (Vogel et al., 2005, Applied Physics B 81, pp. 1015-47). On the other hand, excessively high radiation doses and thus too large cavitation bubbles exert a negative effect on the viability of the target cell resulting subsequently in an increased mortality of the treated cells, which in turns has a deleterious effect on the efficacy of the method.

The application of the optimum radiation dose that ensures effective permeabilization of the cell membrane at the highest possible survival rate thus represents the crucial prerequisite for the success of the method. The optimum radiation dose thus depends to a high degree on the specimen to be irradiated. Depending on the type of cell or tissue, the physiological condition of the cells and the medium or environment surrounding the cells, the laser parameters must be adapted individually in each case, namely a calibration for the laser treatment is needed as is the monitoring of this treatment.

A possible indicator of the effects achieved by the laser application could be the size of the cavitation bubbles formed in which case, as proposed by Vogel et al. (2005, Applied Physics B, 81, pp. 1015-47), the bubble size can be determined by measuring the bubble oscillation time (namely the bubble lifespan). In that publication, the light scattering by the bubbles formed in the laser focus is mentioned as a possible approach to on-line monitoring of the bubble size or bubble lifespan, but it is not described, how this goal is to be achieved.

In DE 103 31 792 A1 is disclosed a laser with dosimetry control whereby the first appearance of bubbles within a tissue can be detected also interferometrically through the change in refractive index. This serves to modulate the laser performance so that the irradiation can be carried out mostly very closely above the bubble formation threshold. In this case, however, only the appearance of the bubbles is detected, and the determination of the lifespan of the bubbles and conclusions drawn therefrom concerning the bubble size are not described.

The dissertation of Jörg Neumann on "Microscopic Studies Concerning Laser-induced Bubble Formation and Bubble Dynamics on Absorbing Microparticles" (University of Lübeck, 2005) deals with linear absorption processes on microparticles (absorbers, for example pigments) such as those taking place in laser therapy of absorbing cell layers, particularly on the ocular fundus. An important objective of this study is to reveal the impact of these particles on the bubble dynamics at different energies of the bubble-inducing radiation. The study discloses the measurement of the lifespan of laser-induced microbubbles by means of the scattering of a test laser beam in the focus of the bubble-induced radiation. In this case, bubbles having a lifespan of about 100 ns are detected. The method, however, is not suitable for use in real time, and no conversion to bubble sizes and thus no complete evaluation of the damage inflicted on the cells by the bubbles is done. Although the dissertation also discusses on-line dosimetry control by the interferometric methods involving back-scattering, the applicability of this control is limited to bubbles with a size in the micrometer-range and is primarily intended for the detection of the appearance of such bubbles.

Whether quantitative measurement of the bubble lifespan by a transmitted radiation method (for example via scattering) in a nominally transparent medium without absorber particles, in which the bubbles are formed individually by muultiphoton absorption and can have a diameter clearly below 100 nm, is at all possible, particularly as a method for on-line monitoring, was hitherto not known.

SUMMARY OF THE INVENTION

It is therefore the object of the invention to provide a method for the optoperforation of single cells by pulsed laser radiation, whereby lie degree of cell membrane permeabilization can be controlled so that the efficiency of foreign body uptake into the irradiated cell is maximal and at the same time the viability of the cells is not unnecessarily impaired.

According to the invention, this objective is reached by use of a method of cell membrane optoperforation, involving the application of laser pulses.

As already mentioned, the uptake of foreign bodies into the cell can be followed by observing the bubble oscillation during the pulsed laser application. Bubble formation does not always occur during laser application, as it is also possible for the plasma formed in the application region as a result of non-linear absorption of laser pulses (particularly free electrons) not to be sufficient to allow the formation of a bubble. Such plasma, however, also destroys chemical bonds in the cell membrane and can, as a result of an accumulation of the effects of many laser pulses, open the cell, so to speak, in a chemical manner. On the other hand, in the event of bubble formation, the local opening of the cell membrane takes place in a thermo-mechanical manner which requires considerably fewer laser pulses.

Moreover, by perforation of the cell membrane using the method of the invention, it is just as possible to discharge substances from the cell or to collapse (chemical) potentials created over the cell membrane. The following remarks therefore refer only, for example, to the application, according to the invention, whereby substances are taken up into the cell.

DETAILED DESCRIPTION OF THE INVENTION

Figure 1:
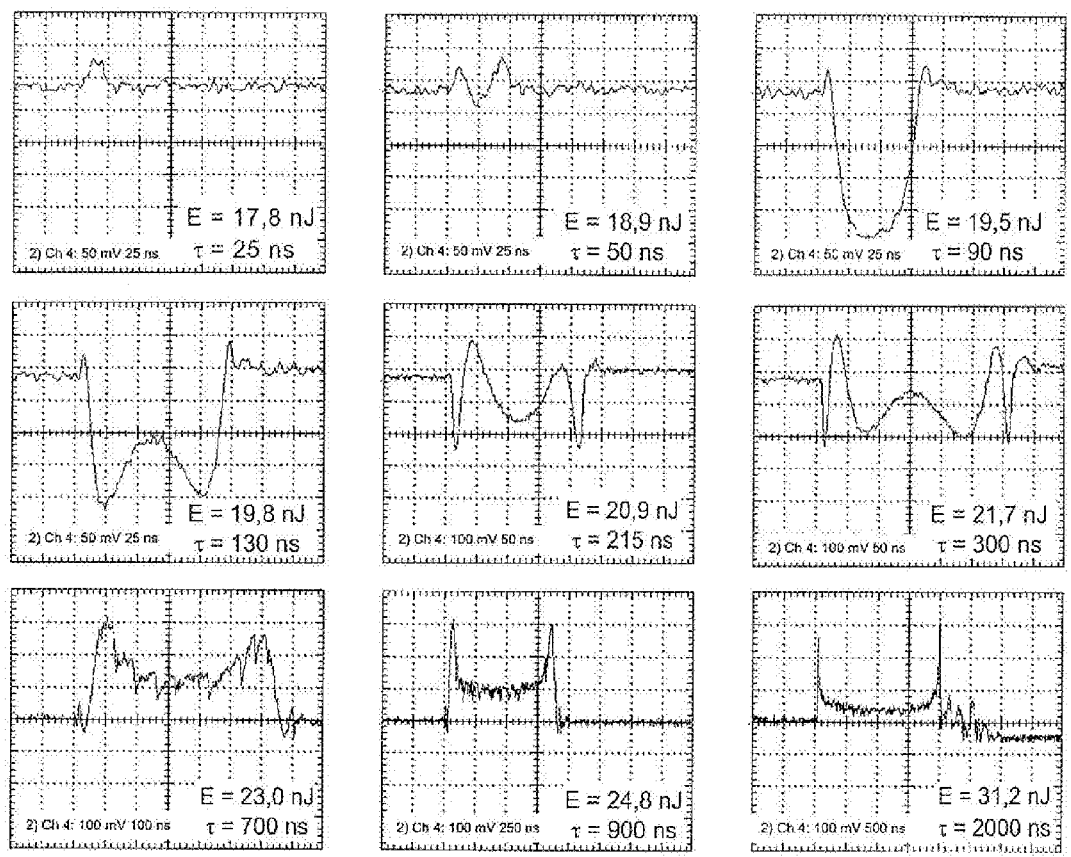
FIG. 1 sets forth a series of graphs representing measured radiation intensity verses time, along with resulting pulse energies and oscillation times.

The invention is based on the understanding that the opening of the cell membrane by single laser pulses or a series of pulses with a repetition rate of <1 MHz always takes place with transient bubble formation in the laser focus. The bubbles then have a lifespan in the range of nanoseconds to microseconds—unlike the long-lived bubbles formed during optoperforation with femtosecond oscillator pulses (repetition rate>1 MHz) in the event of laser overdose.

In the following, it is always assumed that bubble formation is possible. Typical laser parameters that permit this are, in particular, pulse durations in the range of picoseconds to femtoseconds (ps or fs), repetition rates below 1 MHz, preferably about 1 kHz, and pulse energies of the order of magnitude of 1 to 10,000 nJ. Bubble formation during focusing of the pulsed laser onto the cell membrane takes place, when the pulse energy is adjusted to a level sufficient for this to happen. This, however, cannot be achieved by a fixed preselected energy adjustment, because the focus quality (spot size), energy losses on the way and the absorption properties of the target structure differ from case to case. The reproducible creation of bubbles—which ideally should always be of the same size—and thus the same potential for damaging the cell membrane therefore requires an adaptive pulse laser control that is based on the observation of the bubble size. Which size is optimal, depends on the properties of the cell involved.

Hence, according to the invention, bubble formation is continuously monitored and plotted against time. The time interval from the first rise of the bubble to its initial collapse (in the following referred to as the oscillation time) is measured as accurately as possible. This is made possible by the detection of the scattering of a test radiation beam, preferably a test laser beam. The test radiation beam itself should exert no effect on the cells or on the surrounding medium, but should serve only to monitor the optical properties of the material in the pulsed laser focus. Preferably, a low-efficiency cw-laser is used which has a main emission wavelength that differs substantially from that of the pulsed laser. We have found that wavelengths from the near-infrared spectrum, for example 780 nm, are particularly well suited, because they do not interfere with the microscopic observation of the cells.

To this end, the test laser beam must pass through the region of the pulsed laser focus—preferably directly at the cell membrane—in which region the pulsed laser beam brings about the bubble formation. For this reason, it is practical to reflect the test laser beam into the pulsed laser radiation beam. This can be done with a dichroic mirror as can the uncoupling of the test laser beam, after it has passed through the focus. The uncoupled test laser beam is guided to a detector which continuously records the radiation intensity.

The fluctuations of the test laser intensity are attributable to scattering processes in the pulsed laser focus occurring when the bubble oscillates. For very small bubbles, these fluctuations are extremely slight and very short-lasting. To render them at all measurable, the scattering signal of the test laser is detected with a sensitive AC-coupled high-speed photoreceiver (diode with a photocurrent amplifier), preferably one with a signal band width of 25 kHz to 200 MHz. By the AC-coupling, all "slow" (here up to 25 kHz) fluctuations are filtered out of the signal. Such slow fluctuations readily arise from power fluctuations of the test laser or from other external influences. Moreover, the bubble to be detected is often much smaller than the focus volume as a result of which the amount of scattered radiation is considerably smaller than the total intensity of the radiation transmitted through the focus. By AC-coupling, the DC component is removed from the measurement.

Even so, the photoreceiver makes it possible to observe the DC signal as well. This is important for the basic adjustment of the system, because the test laser must be optimally adjusted into the pulsed laser beam which corresponds to a maximal DC signal. The large band width and the sensitivity of the AC photoreceiver make it possible to detect the smallest variations of the scattered-radiation signal of the test laser. The duration of the scattered-radiation signal corresponds to the bubble oscillation time. Because the photoreceiver has a rise and fall time of 1.8 ns, it is suitable for the determination of bubble oscillation times below 5 ns.

The shortest bubble oscillation time measured thus far was 15 ns (at the threshold for bubble formation with femtosecond pulses and focusing with NA=0.9) which corresponds to a bubble radius of only 150 nm. Because of the flexibility of the measuring range, the system is equipped for any possible occurrences (namely for even smaller bubbles at a maximum numerical aperture of the microscope objective of NA=1.3).

FIG. 1 shows a selection of bubble oscillation measurements by the method of the invention as described in the foregoing. All graphs represent the radiation intensity measured vs. time and are provided with information concerning the pulse energies E and the oscillation times $\tau$ resulting therefrom. The bubble oscillations are characterized by significant deviations from the otherwise constant signal course.

The oscillation time of the laser-produced bubbles can be converted into the maximum extensions of the bubbles by means of the Rayleigh equation:

$$R_{max} = T/1.83\sqrt{(p_0-p_v)}/\rho_0$$

Here $p_0$ denotes the hydrostatic pressure in the vicinity of the bubble, $p_v$ the internal bubble pressure and $\rho_0$ the density of the medium.

Figure 2:
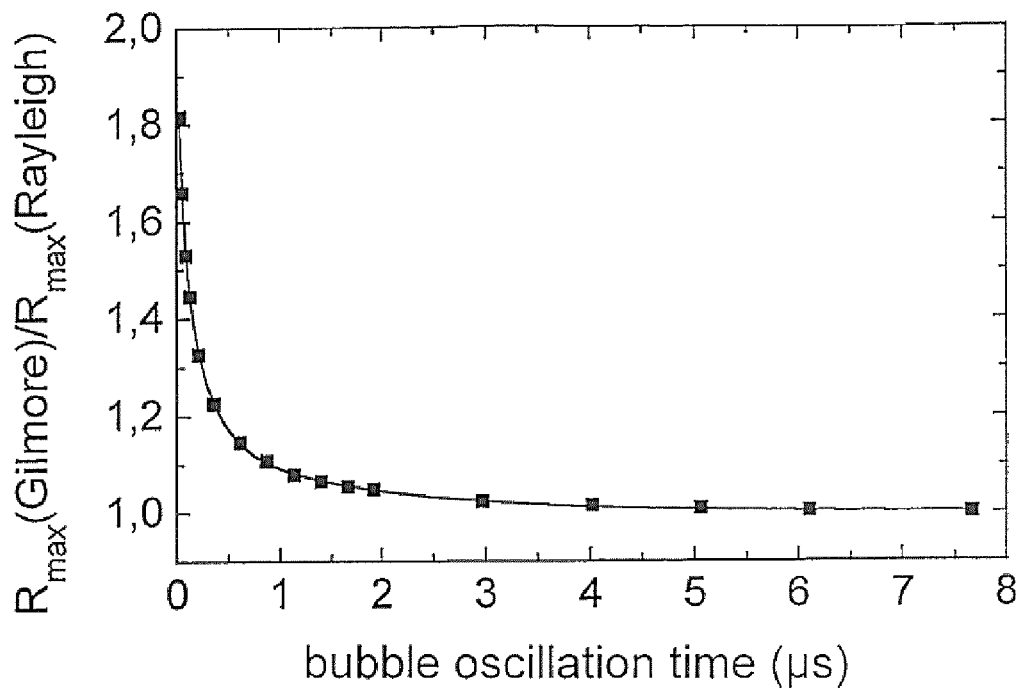
FIG. 2 is a graph showing bubble oscillation time verses maximum bubble extension.

The Rayleigh equation is well known from other technical fields, but is here used for the first time for nanoscale bubbles formed during laser application. We have found that it gives erroneous results because it does not take into account the surface tension. The surface tension σ acts on the bubble as an additional pressure $p=2\sigma/R$, the amplitude of which is inversely proportional to the bubble radius R. This additional pressure changes the relationship between oscillation time and the maximum extension of the bubble. With the aid of the Gilmore model which takes into account the surface tension and its temperature dependence, however, it is possible to calculate correction factors for the Rayleigh equation (to this end refer to FIG. 2). It can be seen from FIG. 3 that the Rayleigh equation particularly underestimates the diameters of very small bubbles and that the Gilmore model shows much better agreement with photographic measurements.

The bubble sizes produced can thus be determined with good approximation from the bubble oscillation times. It is noteworthy in this respect that bubble radii as small as 150 nm have been optically detected, even though the test laser has a markedly greater wavelength. The detection limit of the photodetector with a band width of 200 MHz used here is R≈50 nm.

As already mentioned, other studies have identified the bubble size as a critical factor for the efficiency of foreign body uptake by cells. If the bubbles are too small, they do not sufficiently perforate the cell membrane to ensure the entry of the foreign body, that is to be introduced inside the cell (typically, such bodies consist of nucleic acids, chromosomes, proteins, organelles, dyes, active pharmaceutical agents or functionalized nanoparticles). If, on the other hand, the bubbles are too large, the cell membrane is damaged to such an extent that the cell can no longer recover from the damage and does not survive the treatment. The literature indicates that the upper limit of the bubble diameter suitable for the perforation is between 5 and 7.5 micrometers. Larger bubbles are reported to cause the death of the cells.

The range of the produced bubble diameters that is suitable for a transfection efficiency that is optimal for ensuring the highest possible cell viability cannot be indicated in a universal manner. It depends on the cell type selected, the surrounding medium and also on the kind of foreign bodies to be introduced, because they, too, can react to the laser pulses. This optimal range must be determined for the objective of each individual case. As a rule of thumb, one may assume that the bubble size should be equal to at least the size of the foreign body, but at the most to a fraction of the cell diameter.

The required calibration tests by which, in particular, the success rate of the introduction of the foreign bodies into the cells and the cell viability are studied, where required, even separately, constitute prior art and are commonly used despite being somewhat costly.

Besides the laser pulse energy, the invention provides an additional measurable variable, namely the size of the bubble or the bubble oscillation time for which in the course of the calibration a suitable range can be determined. The special advantage of the invention lies in the continuous measurability of this variable also during the actual treatment procedure. In fact, it is thus not only possible to measure the bubble, actually formed in the pulsed laser focus, practically simultaneously with the pulse: application, but by suitable control of the source of the pulsed laser, the pulsed laser light can be modified to achieve an actively controlled cell-sparing irradiation.

Figure 3:
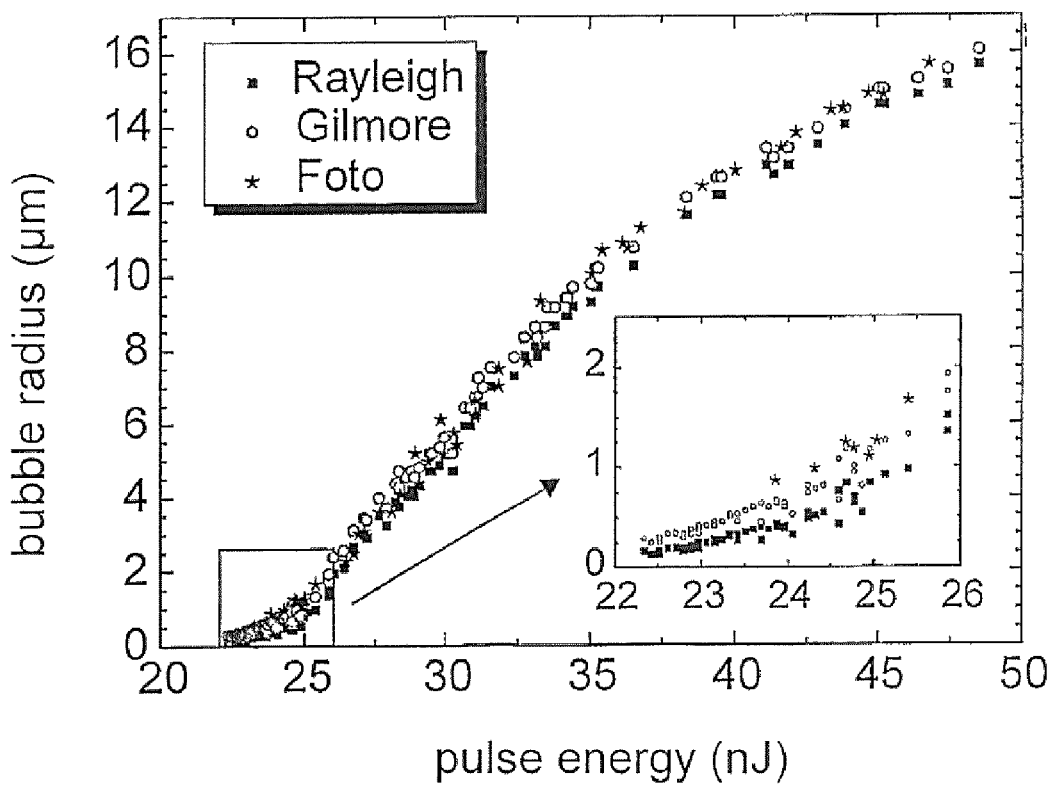
FIG. 3 is a graph showing pulse energy verses bubble radius based on establishes models and equations.

From FIG. 3 it can also be seen that a monotonic relationship exists between the pulse energy of the applied radiation and the observed bubble size. Hence, according to the invention, it is preferable to control the pulse energy of the laser used for the treatment. Although, in principle, this can be done through control of the pump performance or by rotation of a λ/2-plate disposed between polarizers, it is definitely more advantageous to use an acousto-optic modulator because it permits very fast switching.

Automatic control of the optoperforation could be performed as follows:

The laser is directed to the cell membrane or to a preselected site in the vicinity of the cell membrane. A series of laser pulses is now applied for which the energy of the first pulse lies below the previously determined threshold for bubble formation or one known from previous tests. The pulse energy for the following pulses is gradually increased (increasing pulse energy slope), until a preselected bubble size is obtained. The pulse series is then either immediately terminated or it is continued at constant pulse energy until a preselected number of additional pulses that form the desired bubble size has been applied.

Preferably, the foregoing "pulsed laser application strategy" is realized by a suitable computer implementation according to the prior art. In particular, it comprises repeated reading of the AC-photo-detector, the simultaneous interpretation of the measured data concerning the bubble size produced and control of the pulse energy-varying unit, preferably an acousto-optic modulator, based on the program parameters.

Publication DE 103 31 792 A1 discloses the strategy and the equipment for its application. This publication, however, provides no information about the way in which the size of individual bubbles, that are produced, could be determined. DE 103 31 792A1 deals with the laser treatment of tissue layers and, hence, with the simultaneous irradiation of a large number of very different cells so that, in that case, such a question does not arise directly.

The optoperforation of certain single cells thus places higher requirements on dosimetry control. The bubble size appropriate for this purpose must and can be determined much more accurately and reproducibly than this has thus far been possible according to the prior art.

Finally, it should be mentioned that the use of the Rayleigh equation and/or the corrections of the Gilbert model are not absolutely necessary to attain operable dosimetry control. To this end, the measurement of the bubble oscillation time alone is entirely sufficient, provided the method is calibrated for the oscillation time. The conversions into bubble sizes have been and are, however, very useful for the understanding of the effects achieved and naturally can also be calculated and recorded for the adaptive control of the pulsed laser without major expense. It may be advantageous to use these determined bubble sizes in conjunction with, for example, the information about the cell type treated to achieve an algorithmic optimization of laser control, for example, to accelerate the increase in pulse energy slope.

The invention claimed is:

1. A method for optoperforation of a cell membrane by application of laser pulses, comprising:
    focusing a pulsed laser onto a cell membrane of a cell to be perforated,
    applying by the pulsed laser a series of laser pulses of predetermined pulse energy to the cell membrane, thereby causing cavitation bubbles on the cell membrane to be formed within a focus of the pulsed laser,
    transmitting by a probe laser a probe laser beam through the focus of the pulsed laser,
    detecting fluctuations in an intensity of the probe laser beam,
    measuring, based on the fluctuations, an oscillation time of said cavitation bubbles formed in the focus of the pulsed laser, and controlling, based on the oscillation time, a pulse energy of the pulsed laser to a level at which the oscillation time of the cavitation bubbles attains a predetermined value.

2. The method according to claim 1, wherein only fluctuations in the transmitted probe laser beam intensity, lasting less than 40 microseconds are detected.

3. The method according to claim 2, wherein a cw-laser with a main emission wavelength from the near-infrared (NIR) spectrum is used to produce the probe laser beam.

4. The method according to claim 2, further comprising, prior to the steps of claim 2, determining the oscillation time required for a certain cell type and/or a certain substance to be taken up by the cell as a function of the viability of the cell by applying a series of laser pulses of predetermined pulse energy.

5. The method according to claim 2, wherein the laser pulses of the pulsed laser are in a picosecond-range or femtosecond-range and applied at a repetition rate of less than 1 MHz.

6. The method according to claim 2, wherein the predetermined pulse energy during application of the series of laser pulses is changed from pulse to pulse by controlling an acousto-optic modulator through which the series of laser pulses passes.

7. The method according to claim 1, wherein a cw-laser with a main emission wavelength from the near-infrared (NIR) spectrum is used to produce the probe laser beam.

8. The method according to claim 7, further comprising, prior to the steps of claim 3, determining the oscillation time required for a certain cell type and/or a certain substance to be taken up by the cell as a function of the viability of the cell by applying a series of laser pulses of predetermined pulse energy.

9. The method according to claim 7, wherein the laser pulses of the pulsed laser are in a picosecond-range or femtosecond-range and applied at a repetition rate of less than 1 MHz.

10. The method according to claim 7, wherein the predetermined pulse energy during application of the series of laser pulses is changed from pulse to pulse by controlling an acousto-optic modulator through which the series of laser pulses passes.

11. The method according to claim 1, further comprising, prior to the steps of claim 1, determining the oscillation time required for a certain cell type and/or a certain substance to be taken up by the cell as a function of the viability of the cell by applying a series of laser pulses of predetermined pulse energy.

12. The method according to claim 11, wherein the laser pulses of the pulsed laser are in a picosecond-range or femtosecond-range and applied at a repetition rate of less than 1 MHz.

13. The method according to claim 11, wherein the cell to be optoperforated is disposed in a medium containing a substance which is to be taken up into the cell to be optoperforated and said substance is selected from the group consisting of nucleic acids, chromosomes, proteins, organelles, dyes, active pharmaceutical agents and functionalized nanoparticles.

14. The method according to claim 1, wherein the laser pulses of the pulsed laser are in a picosecond-range or femtosecond-range and applied at a repetition rate of less than 1 MHz.

15. The method according to claim 14, wherein the repetition rate amounts to about 1 kHz.

16. The method according to claim 1, wherein the predetermined pulse energy during application of the series of laser pulses is changed from pulse to pulse by controlling an acousto-optic modulator through which the series of laser pulses passes.

17. The method according to claim 1, wherein the predetermined pulse energy of the series of laser pulses applied by the pulsed laser is between 1 and 10,000 nJ.

18. The method according to claim 1 wherein, after measuring the oscillation time to attain the predetermined value, a predetermined number of pulses is applied by the pulsed laser to the cell membrane.

19. The method according to claim 1, wherein the cell is disposed in a medium containing a substance which is to be taken up into the cell and which is selected from the group consisting of nucleic acids, chromosomes, proteins, organelles, dyes, active pharmaceutical agents and functionalized nanoparticles.

* * * * *